(12) United States Patent
Kraus

(10) Patent No.: US 6,311,339 B1
(45) Date of Patent: Nov. 6, 2001

(54) URINE COLLECTION APPARATUS AND METHOD

(76) Inventor: John D. Kraus, 1854 Home Rd., Delaware, OH (US) 43015

( * ) Notice: Subject to any disclaimer, the term of this patent is extended or adjusted under 35 U.S.C. 154(b) by 0 days.

(21) Appl. No.: 09/648,388

(22) Filed: Aug. 25, 2000

(51) Int. Cl.⁷ .................................................. A47K 11/00
(52) U.S. Cl. ............................................. 4/144.3; 4/144.1
(58) Field of Search ................... 4/144.3, 144.1, 4/431, 301; 15/421, 419

(56) References Cited

U.S. PATENT DOCUMENTS

| | | | |
|---|---|---|---|
| 1,106,231 | * 8/1914 | Marshall | 15/421 |
| 1,742,810 | * 1/1930 | Hosking | 15/421 |
| 2,176,139 | * 10/1939 | Lofgren | 15/421 |
| 2,295,817 | * 9/1942 | Winther | 15/421 |
| 2,490,969 | * 12/1949 | Kinyon | 4/144.3 |
| 2,658,046 | 11/1953 | Duke . | |
| 3,039,463 | * 6/1962 | Dickey, Jr. et al. | 15/421 |
| 3,114,916 | 12/1963 | Hadley . | |
| 3,440,681 | * 4/1969 | Hixson et al. | 15/421 |
| 4,164,795 | * 8/1979 | Johnson | 4/144.1 |
| 4,194,508 | * 3/1980 | Anderson | 4/144.3 |
| 4,202,058 | 5/1980 | Anderson . | |
| 4,345,341 | * 8/1982 | Saito | 4/144.3 |
| 4,360,933 | * 11/1982 | Kimura et al. | 4/144.3 |
| 4,747,166 | * 5/1988 | Kuntz | 4/144.1 |
| 5,768,748 | * 6/1998 | Silvera et al. | 15/421 |
| 5,894,608 | 4/1999 | Birbara . | |

* cited by examiner

Primary Examiner—David J. Walczak
Assistant Examiner—Khoa Huynh
(74) Attorney, Agent, or Firm—Mueller and Smith LPA

(57) ABSTRACT

A urine collection apparatus and method employing a collector which receives liquid urine within a well component accessed by a flexible urine collection conduit. The extent of vacuum for placement and retention is adjusted with an upwardly disposed vacuum control orifice, while urine is collected in a well portion of the collector.

20 Claims, 5 Drawing Sheets

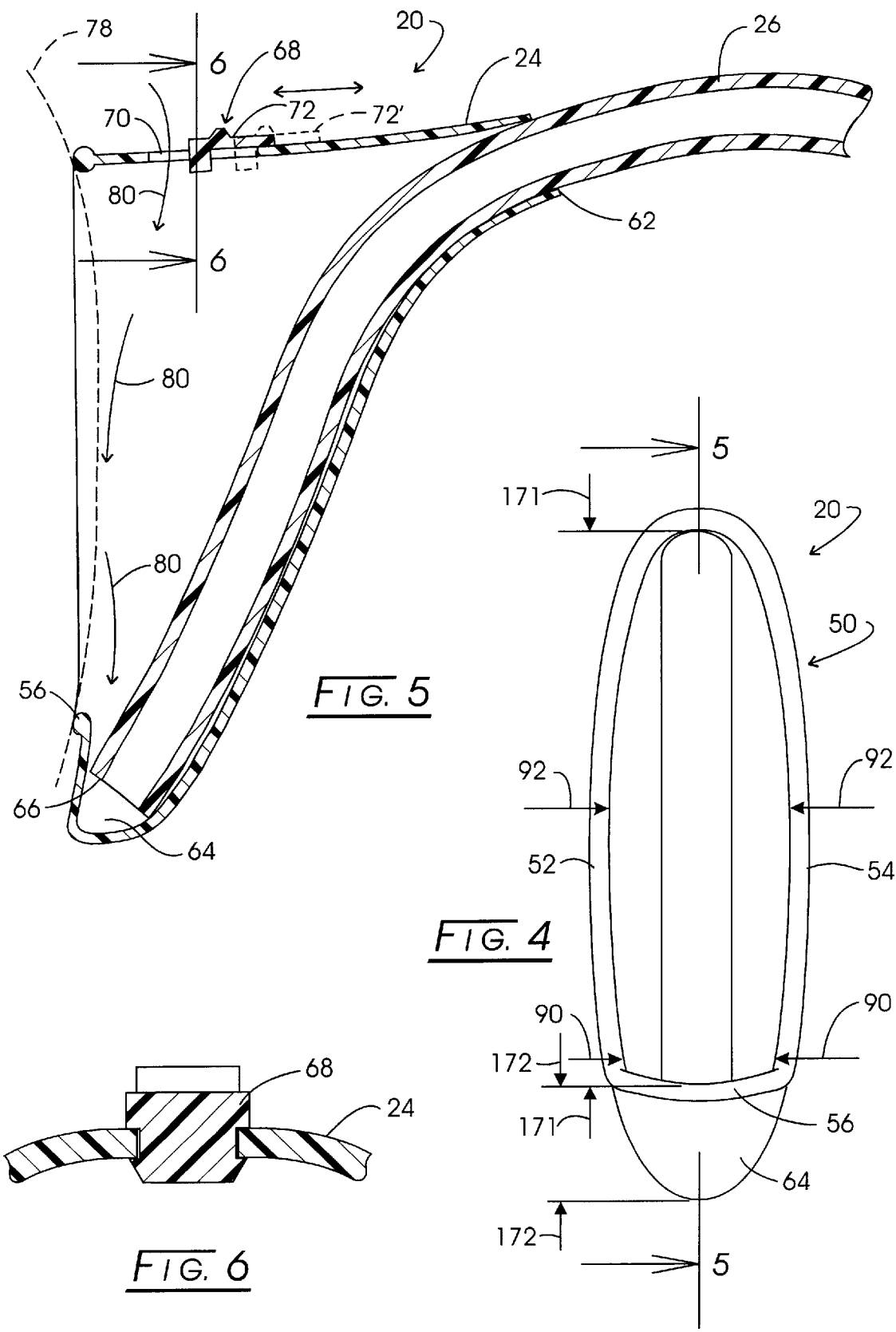

URINE COLLECTION APPARATUS AND METHOD

CROSS-REFERNCE TO RELATED APPLICATIONS

Not applicable.

STATEMENT REGARDING FEDERALLY SPONSORED RESEARCH

Not applicable.

BACKGROUND OF THE INVENTION

Accommodating the physiological necessity to urinate on the part of incapacitated or infirm patients is problematical. Proposed solutions to this need have demonstrated that it is an illusive problem.

The ubiquitous bedpan generally has been employed for this procedure. However, where the patient is severely incapacitated, for example, in recovery from stroke and the like, the procedure is highly physically taxing both on the part of the patient and the medical attendant.

Vacuum assisted devices have been proposed for the collection of urine. These devices generally are described as being positioned about the urethra. While such systems promise a desirable convenience, their designs therefore have exhibited technical difficulties. For example, in one approach, the vacuum is utilized to create a urine air entrainment which then is delivered by suitable conduits to a collection facility such as a tank. Aeration procedures, however, lead to difficulties in the collection by evoking frothing and contamination of the vacuum source due to the entrained nature of the urine. The vacuum assisted devices also have proven difficult to position because of the vacuum induced attachment of the entryway of the collecting device with the skin of the patient. While some vacuum may be desirable for this positioning procedure, the vacuum requisite to urine removal is one posing a considerable hindrance to proper placement. In general, following placement of the collection vessel, the vacuum should fully support the collector throughout the urination procedure.

BRIEF SUMMARY OF THE INVENTION

The present invention is addressed to apparatus and method for collecting urine, such apparatus being particularly suited for utilization with those physically handicapped. A polymeric collector component is employed which is configured with a collection cavity extending outwardly from a lip. That lip is configured to engage and support a vacuum coupling with the skin, for example, at the labium region. Extending integrally downwardly from the lower region of the lip is a well which functions to collect urine while avoiding its aspiration or air entrainment. A urine collection conduit is provided which is formed preferably of a flexible transparent polymeric material. It is coupled with the collector and incorporates a collection opening located within the well. The oppositely disposed urine expulsion end of this conduit extends into the urine input port of a urine collection tank at a location adjacent the internal sidewall of the tank to promote a surface tension defining relationship between expelled urine and the side of the tank. This arrangement functions to avoid undesirable foaming of the urine within the collection cavity of the tank. A vacuum is imposed within the tank, and thus, is transferred to the collection component utilizing a vacuum assembly.

In a preferred arrangement, the top wall portion of the collector incorporates a vacuum control orifice which is manually adjustable by an attendant to provide an air entry opening of first extent which is selected to facilitate the positioning of the lip component of the collector for urine collection. Following such positioning, the control orifice is adjusted to provide an air opening of second extent less than the first extent and this opening functions to create a vacuum coupling of the collector with surrounding skin or the labium. The opening further functions to dry the skin region enclosed by the collector. In this regard, the termination of urination may be observed through the transparent collection conduit and the vacuum operated system may be continued in operation as an afterflow to carry out such drying activities.

Other objects of the invention will, in part, be obvious and will, in part, appear hereinafter.

The invention, accordingly, comprises the apparatus and method possessing the construction, combination of elements, arrangement of parts and steps which are exemplified in the following detailed description.

For a fuller understanding of the nature and objects of the invention, reference should be had to the following detailed description taken in connection with the accompanying drawings.

BRIEF DESCRIPTION OF THE DRAWINGS

FIG. 4 is a front view of the collector of the invention showing its lip configuration;

FIG. 5 is a sectional view of the collector of the invention additionally showing a collection conduit positioning;

FIG. 6 is a sectional view taken through the plane 6—6 in FIG. 5;

DETAILED DESCRIPTION OF THE INVENTION

Figure 1:
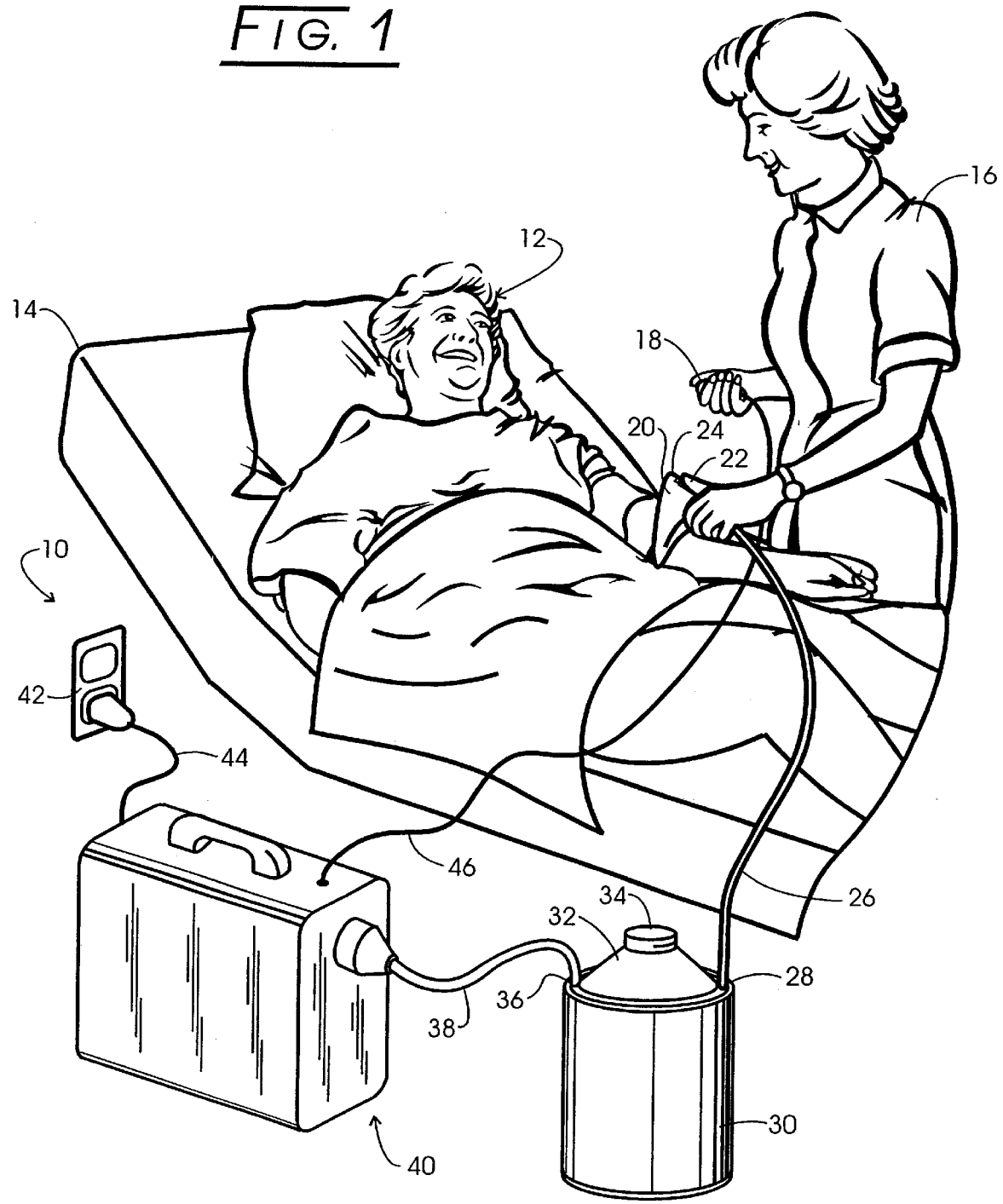
FIG. 1 is a perspective view showing the components of the apparatus of the invention.

Referring to FIG. 1, the apparatus and methodology of the invention is represented in perspective in general at 10 as employed in conjunction with a patient 12 in a reclining position upon a bed 14. In the figure, a medical attendant 16 is seen holding an on and off switch 18 in her right hand and a rigid polymeric collector 20 in her left hand. Note that the thumb 22 of the attendant 16 is extending over the top wall portion 24 of the collector 20.

From the collector 20, there extends a urine collection conduit 26 which will be seen to have a collection opening extending into the collector 20 and a urine expulsion end or opening which extends through a urine input port 28 of a urine collection tank 30. Tank 30 preferably is formed of a rigid material suited for retaining a vacuum. In this regard, the tank 30 may be formed of steel and is additionally configured having a conical top surface 32 extending to a removable cap 34. This arrangement facilitates the emptying of the tank 30 which, for example, will have a capacity of 10 to 20 liters. Although the urine voided during a night by a typical patient is only a liter or so, the larger the tank 30, the more effective the urine-air separation. Disposed diametrically oppositely from the urine input port 28 is a vacuum port 36 through which extends a vacuum conduit 38. Conduit 38 forms part of a vacuum assembly represented generally at 40 which is powered from a typical wall outlet 42 as represented by line 44 and is actuated between on and off states by connection of line 46 with switch 18. Apparatus 40 preferably will be a driven fan device capable of developing a vacuum of about 10 kilopascals at the collector 20. A prototype of the apparatus 10, for example, utilized a conventional lightweight portable vacuum cleaner. In particular, a type C 2094 Commercial Portapower vacuum cleaner manufactured by the Hoover Company of North Canton Ohio was successfully employed.

With the arrangement 10, it is preferred that the attendant 16 be readily apprised of the commencement and termination of urination by the patient. This feature is developed by forming the conduit 26 of a flexible transparent polymeric material. Preferably, the size of conduit 26 will exhibit about a one half inch outer diameter. Correspondingly, conduit 38 may be that size or of a larger diameter. For example, up to about one inch.

In general, the materials utilized for the collector 20 should be somewhat rigid to sustain vacuum conditions and have a capability of withstanding the chemical attack of urine. In the latter regard, urine is a fluid excreted by the kidneys, passed through the ureters, stored in the bladder and discharged through the urethra. The average quantity of urine excreted under ordinary dietary conditions in twenty-four hours is about 1000 to 2000 ml. The fluid has a specific gravity of about 1.024, varying from 1.005 to 1.030. One thousand parts of healthy urine contain about 960 parts of water and 40 parts of solutes, which consists chiefly of urea, 23 parts; sodium chloride, 11 parts; phosphoric acid, 2.3 parts; sulfuric acid, 1.3 parts; uric acid, 0.5 parts; also hippuric acid, leukomaines, urobilin, and certain organic salts. Materials suited for the collector 20 thus will include polyamines, acrylic resins, vinyl resins, polycarbonates and polyolefins. Conduit 26 typically is formed of a transparent flexible polyvinyl chloride. Such transparency permits the attendant 16 to observe both the commencement and termination of urination. In general, the switch 18 is activated to turn off the vacuum deriving apparatus 40 about 20 seconds following an observation of the termination of urination. This provides for a drying action of air moving through the collector 20.

Figure 2:
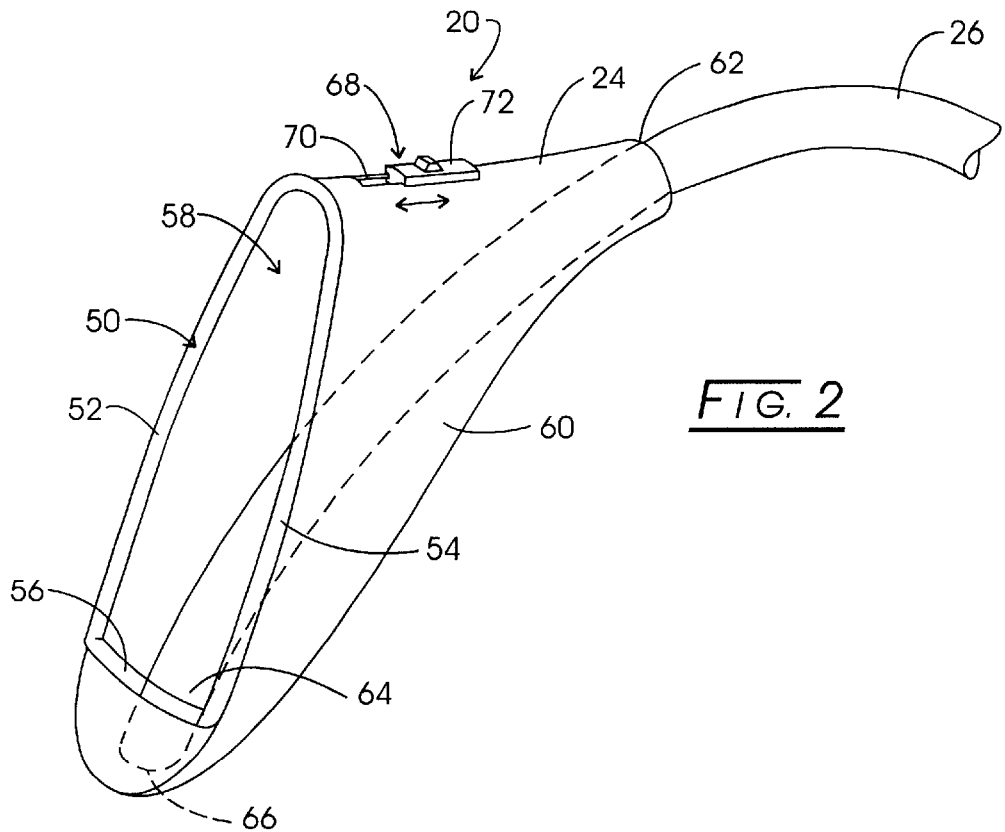
FIG. 2 is a perspective view of a collector and associated collection conduit employed with the apparatus of the invention.

Referring to FIG. 2, the structuring of the collector 20 is revealed in perspective fashion. The device 20 is generally "nose"-shaped, being formed of the noted relatively rigid plastic and having a continuous lip 50 which is seen to be shaped generally in the fashion of a truncated ellipse. The widthwise separation of the two sides 52 and 54 of the lip 50 is important in that the lip must surmount the urethra and engage skin which is adjacent thereto. In this regard, the urethra is present in both the male and female and is a membranous canal conveying urine from the bladder to the exterior of the body. The female urethra is a canal of about 3.7 cm length extending from the neck of the bladder, running above the anterior vaginal wall and piercing the urogenital diaphragm to reach the urinary meatus. Correspondingly, in the male, the urethra is a canal extending from the neck of the bladder to the urinary meatus, measuring about 20 cm in length. Note that the lower component 56 of the lip 50 functions to define the truncate portion of the ellipse profile. For a female embodiment, the lip component is intended to engage and establish vacuum with the labium, a fleshy border or edge used in anatomical nomenclature as a general term to designate such a structure. Extending outwardly from the lip 50 is a collection cavity represented generally at 58 into which urine will be expressed. The cavity 58 is developed by the sidewall 60 of the collector 20 and it may be noted that the integrally formed top wall portion 24 extends to a tube supporting opening 62.

An important operational feature of the collector 20 resides in a design which is developed for the purpose of maintaining the urine in non-air entrained liquid form. This operational feature is achieved through the utilization of a downwardly disposed urine collection well 64. In this regard, note that the urine collection conduit 26 extends through the opening 62 such that its urine input port 66 is positioned within the well 64. Thus, when suction is introduced from the conduit 26, liquid urine is readily removed. As noted above, it is preferred that the conduit 26 be formed of a transparent polymeric material such that the attendant will be apprised as to the commencement and termination of the act of urination.

FIG. 2 further reveals the presence of a vacuum control orifice represented generally at 68 which, for the present embodiment, is configured as a slot 70 within which a valve slide member 72 may be manipulated to adjust the extent of the air entry opening represented by block 70. With this arrangement, the amount of vacuum may be adjusted by the attendant by hand manipulation of this slide member 72.

Figure 3:
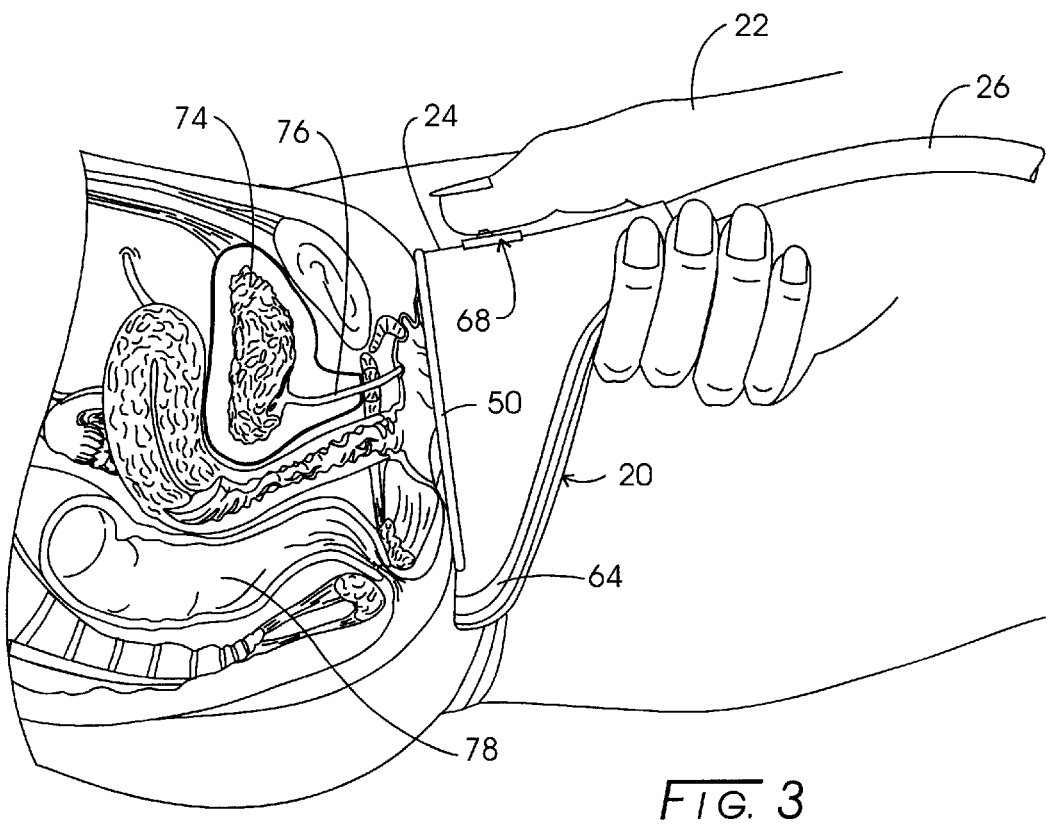
FIG. 3 is a partial sectional view showing the positioning of the collector of the invention.

FIG. 3 reveals the placement of collector 20 with respect to a female urine collection procedure. In the figure, the bladder is represented at 74, the urethra at 76 and colon at 78. The lip 50 is seen positioned against the labium and, in the course of this positioning procedure, the thumb 22 of the attendant adjusts the slide 72 of the vacuum control orifice 68 such that a lesser vacuum, for example, of about 5 kPa is present. When placement is completed, then the slide member 68 is pushed forwardly to reduce the extent of the air entry opening and, thus, increase the vacuum retention of the lip 50 against the labium, Referring to FIGS. 4 and 5, a more detailed representation of the collector 20 and associated urine collection conduit 26 is presented. The long dimension of the collector 20 opening represented by the dimensional arrows 171 is typically 9 or 10 cm and the vertical dimension of the lip 64 represented by the dimensional arrows 172 is typically 20 or 30 mm. Note that the urine input port 66 of the conduit 26 extends into the wall 64 such that urine is removed as a fluid through this transparent flexible tube. Tube 26 is seen to be supported at the opening 62. The figure reveals that the lip 50 is in position against the labia represented as a dashed outline 78. An alternate positioning of the vacuum control orifice 68 is shown in the drawing. In this regard, the air entry opening 70 is shown partially closed by the slide member 72 which is oriented to develop a retention vacuum as opposed to a positioning vacuum condition. For the latter arrangement, the slide member 72 is moved rearwardly by the attendant to the position shown in phantom at 72'. FIG. 6 reveals a cross-section of this slide member 68 as it is slidably mounted within the top wall portion 24. With the arrangement of the invention, following a termination of urination as observed by the attendant in viewing the transparent tube or conduit 26, the vacuum is maintained for about a twenty second interval to create an airflow as represented at arrows 80, functioning to dry the region adjacent the urethra. Of course, the transparent conduit 26 also prevents a premature removal of the collector 20 from its operative position.

For the female embodiment of the collector 20, the dimensions of the opening formed by the lip 50 have been found to be of importance. Looking to FIG. 4, the dimension of the opening defined by the lip 50 at the lower component 56 preferably will be about 25 to 30 mm. This dimension is represented by the dimensional arrow 90. Additionally, the mid position separation of the lip components 52 and 54 as represented at dimension arrows 92 will be about 30 to 40 mm.

Figure 7:
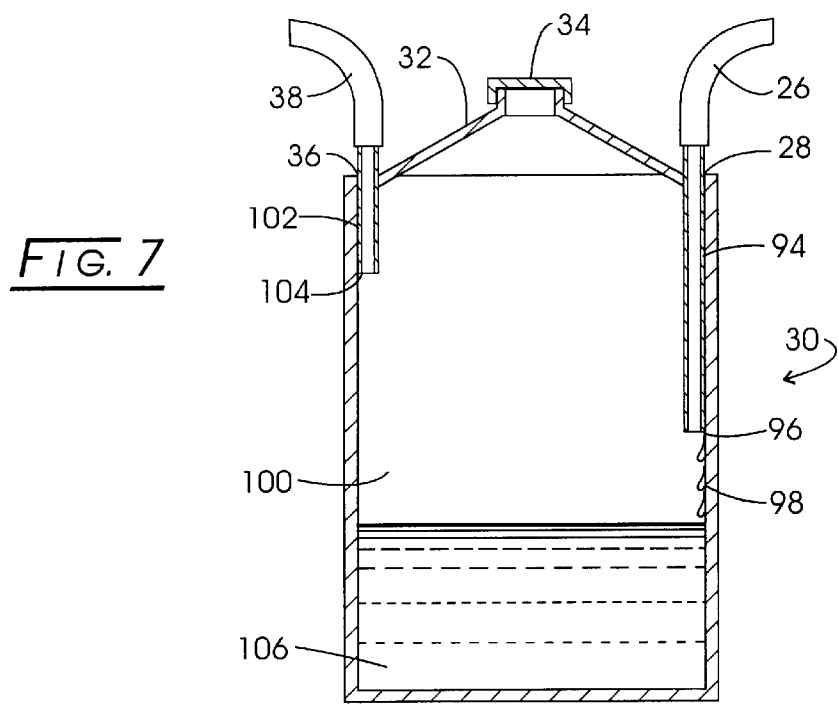
FIG. 7 is a sectional view of a collection tank employed with the apparatus of the invention.

Turning now to FIG. 7, the configuration of the urine collection tank 30 is revealed. Because of the vacuum involved with the apparatus, the tank 30 should be formed of a rigid material, for example, steel. Its capacity may, for example, be of about ten gallons to permit the arrangement of the invention wherein the urine is retained in liquid form without air entrainment or frothing. In the figure, the urine input port 28 again is reproduced through which a rigid extension tube or conduit 94 extends to a urine expulsion end 96. Note that this expulsion end is located adjacent the normally upstanding internal sidewall 98 of the collection tank 30. This position of adjacency with the internal sidewall 98 is to an extent effective to evoke a surface tension of urine expelled from the opening 96 against the wall 98. With that arrangement, a promotion of liquid consistency is effected.

A vacuum is evoked within the cavity 100 of tank 30 from the vacuum conduit 38 as it extends through the vacuum port 36. In this regard, a rigid polymeric pipe or the like 102 is seen to be coupled to the flexible conduit 36 and extends to an air intake opening 104. Note that the opening 104 is positioned diametrically opposite the corresponding expulsion end 96 of tube 94 and is at a higher elevation within the tank than the end 96 to avoid ingress of urine into the vacuum apparatus. As is apparent, the urine 106 collected in the tank 30 is removed by the opening of cap 34. A pouring spout may be connected at the opening for this purpose.

Figure 8:
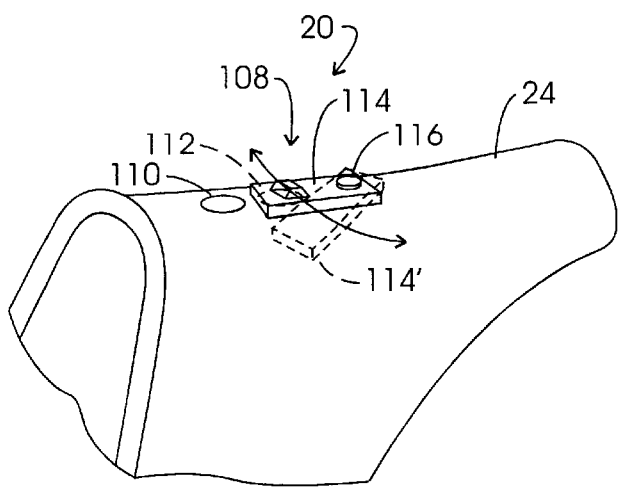
FIG. 8 is a partial perspective view showing another embodiment of a vacuum control orifice.
Figure 9:
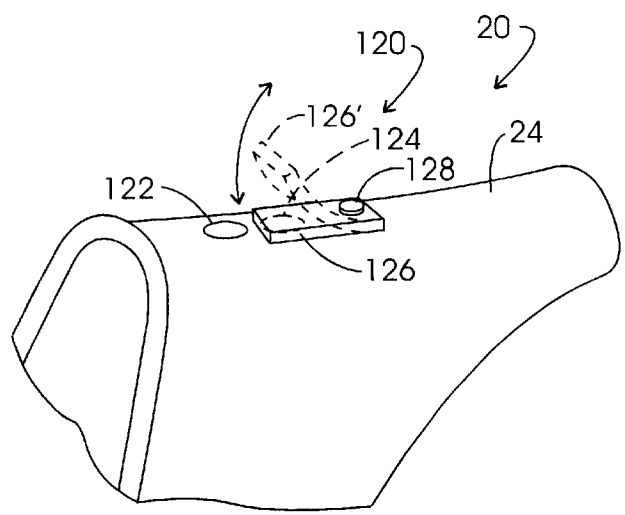
FIG. 9 is a partial perspective view showing still another embodiment of a vacuum control orifice employed with the apparatus of the invention.

FIGS. 8 and 9 reveal alternate arrangements for the vacuum control orifice positioned at the top wall portion 24 of collector 20. In FIG. 8, the vacuum control orifice represented generally at 108 is configured with two arrow intake openings 110 and 112 which, when combined, provide a combinational opening of initial extent for positioning of collector 20. The air intake openings 110 and 112 are typically 5 to 8 mm in diameter. Both may be the same size or one larger or smaller than the other. To provide for this positioning orientation, a rigid closure bar 114 is moved to the orientation shown in phantom at 114'. Following placement, then the retention vacuum is developed by moving the closure bar 114 to the orientation shown in solid line fashion.

FIG. 9 reveals a vacuum control orifice 120 within top wall 24 which incorporates two air intake openings 122 and 124. However, for this embodiment, a flexible flap valve 124 is connected by rivet 128 to top wall 24 and is flexibly manipulated from a position shown in solid line fashion covering the opening 124 to the upwardly flexed orientation shown in phantom at 126' for evolving a positioning vacuum condition.

Figure 10:
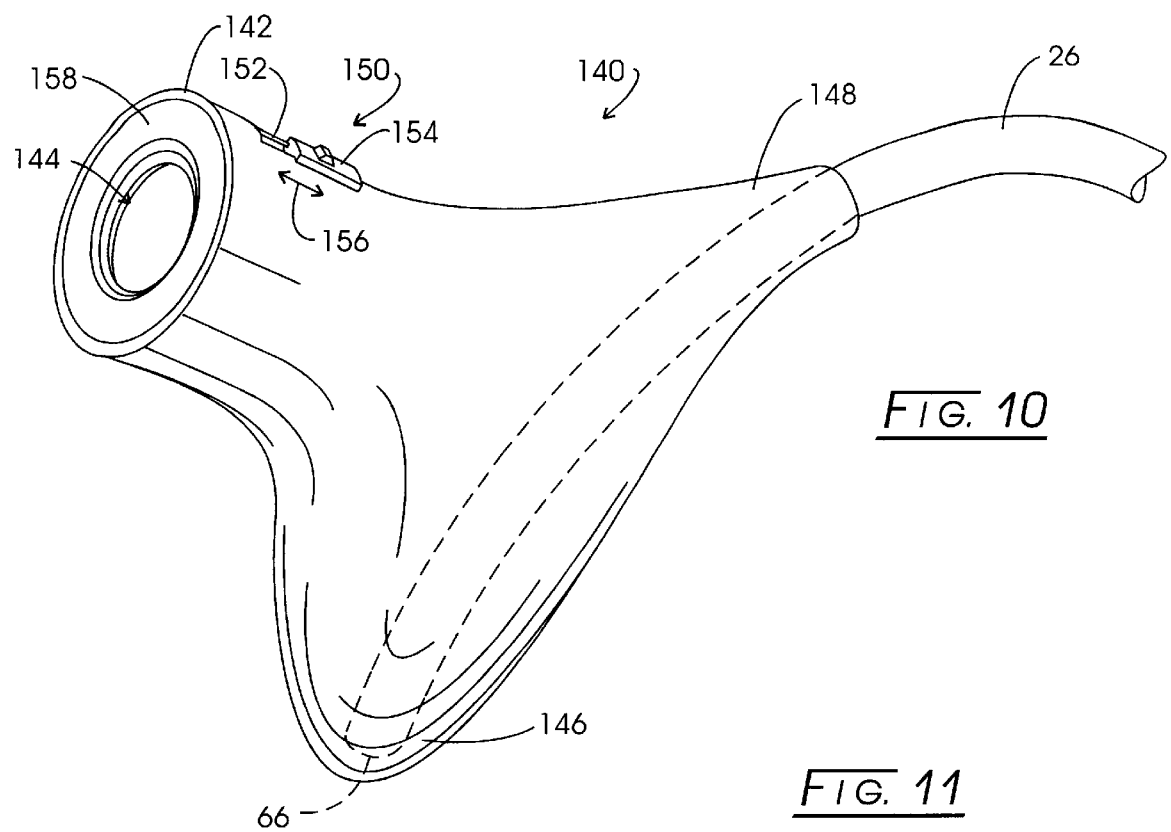
FIG. 10 is a perspective view of a collector according to the invention representing a male counterpart.
Figure 11:
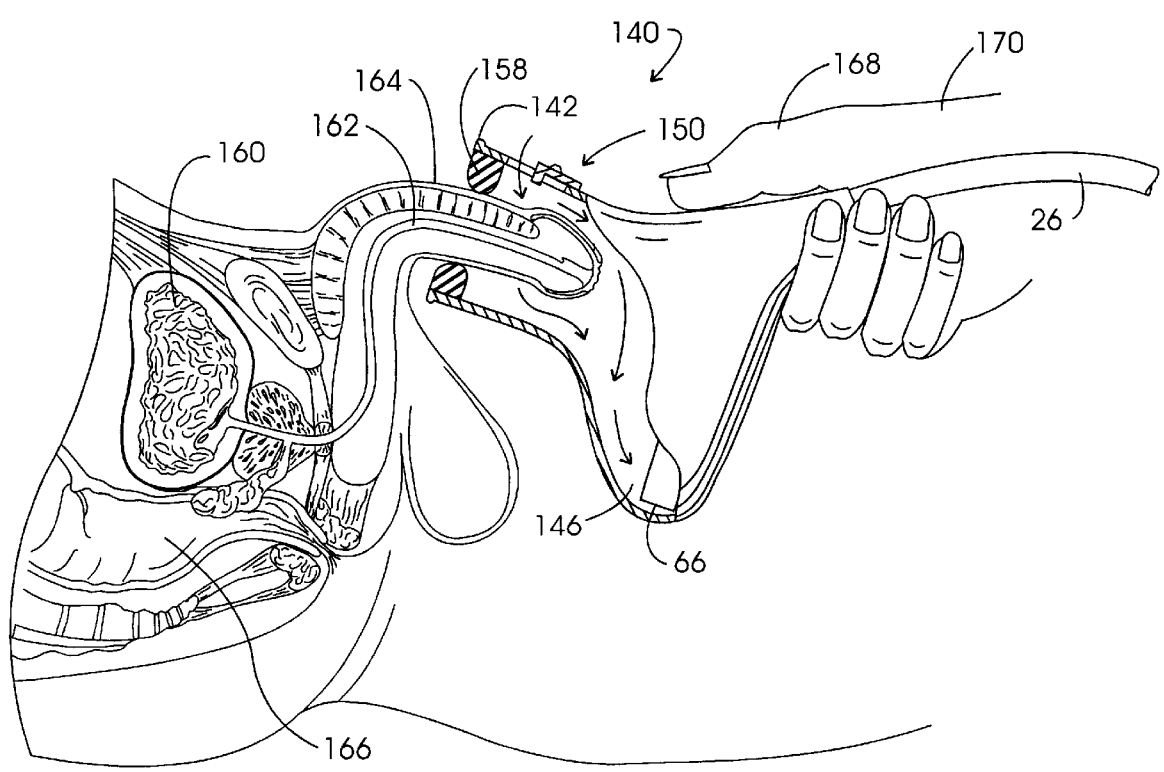
FIG. 11 is a partial sectional view showing the utilization of the collector in FIG. 10.

FIGS. 10 and 11 illustrate the male counterpart of the collector component of the apparatus of the invention. In FIG. 10, the collector is represented in general at 140 in conjunction with the earlier-described urine collection conduit which again is numbered 26. The collector 140 is configured with a continuous ridge 142 and extends outwardly therefrom to define an internal collection cavity represented generally at 144. Cavity 144 extends to a lower disposed well 146 into which the collection opening 66 of conduit 26 extends as in the earlier embodiment. As before, the top wall portion 148 of collector 140 is configured with a vacuum control orifice represented generally at 150. Orifice 150 is configured with a slot communicating in air supply relationship with the cavity 144 as represented at 152. Slot 152 is selectively opened and closed by a slide valve component 154 which is slidably moveable as represented by the dual arrow 156. Note, additionally, the presence of a lip defining soft rubber annulus 158 extending within the ridge 142. This annulus 158 functions to secure a vacuum about the penis and promote its insertion into cavity 144, while the orifice 150 is adjusted to facilitate such insertion. This arrangement is revealed in FIG. 11 wherein the bladder is represented at 160; the urethra at 162 extending through the penis 164. The colon is represented at 166. Adjacent the orifice 150 is the thumb 168 of hand 170 of an attendant.

As before, the collection conduit 26 preferably is formed of a flexible transparent polymeric material and extends to a collection tank as described earlier at 30 (FIGS. 1 and 7), which tank is, in turn, is coupled with a vacuum assembly as described at 40 (FIG. 1). In general, the application of vacuum or low pressure within the collection cavity as at 144 as well as with the corresponding cavity of the female counterpart has been found to be beneficial in aiding patient urination.

Since certain changes can be made in the above apparatus and method without departing from the scope of the invention herein involved, it is intended that all matter contained in the above description or shown in the accompanying drawings shall be interpreted as illustrative and not in a limiting sense.

What is claimed is:

1. Apparatus for collecting urine from a body, comprising:

a collector having a continuous lip configured to surmount the urethra and engage skin adjacent thereto in urine collecting relationship;

said collector including a collection cavity extending outwardly from said lip having a top wall portion, and a liquid urine collection well generally oppositely disposed from said top wall portion and extending below said lip in fluid flow communication with said collection cavity, said top wall portion being configured defining an air entry opening for admitting air to promote urine collection and drying of skin wetted by urine;

a urine collection tank having an internally disposed normally upstanding side wall, a urine input port, a vacuum port and a removable upwardly disposed liquid disposal assembly;

a urine collection conduit having a collection opening positioned for collecting urine from said well at a location within said well effective to collect said urine substantially as a liquid and having a urine expulsion end extending through said urine input port; and a vacuum assembly including a vacuum conduit having an air intake opening extending through said collection tank vacuum port spaced from said urine collection conduit urine expulsion end.

2. The apparatus of claim 1 in which said collector is configured to provide said air entry opening as a vacuum control orifice positioned outwardly from said lip at said top wall portion, having an opening of first extent selected to facilitate the positioning of said lip in contacting adjacency with the skin adjacent said urethra and adjustable to exhibit an opening of second extent less than said first extent effective to derive vacuum coupling of said lip against said skin.

3. The apparatus of claim 2 in which said opening first extent is effective to derive a vacuum within said collection cavity of about 5 kilopascals.

4. The apparatus of claim 2 in which said opening second extent is effective to derive a vacuum within said collection cavity of about 10 kilopascals.

5. The apparatus of claim 2 in which said vacuum control orifice comprises:

first and second openings exhibiting said first extent; and a manually actuable valve moveable over said second opening to derive said second opening extent.

6. The apparatus of claim 5 in which said manually actuable valve is a flexible flap valve.

7. The apparatus of claim 5 in which said manually actuable valve is a slide valve movable within a slot-shaped said air entry opening between a first position exhibiting said opening of first extent and a second position exhibiting said opening of second extent.

8. The apparatus of claim 5 in which said manually actuable valve comprises a rigid closure bar having one end pivotally mounted upon said collector top portion.

9. The apparatus of claim 1 in which said lip exhibits a generally truncated ellipse profile having a widthwise opening extent adjacent said well of about 25 to 30 mm, said well being located downwardly from the truncated portion of said profile.

10. The apparatus of claim 1 in which said urine collection conduit is formed of a flexible polymeric material having a transparency effective to permit visual monitoring of the passage of urine therethrough to determine the termination of urine flow.

11. The apparatus of claim 1 in which said urine collection conduit extends within said urine collection tank to an extent wherein said urine expulsion end is below said vacuum assembly air intake opening and in adjacency with said internal sidewall.

12. The apparatus of claim 11 in which said urine expulsion end is positioned in adjacency with said sidewall to an extent effective to evoke a surface tension of urine expelled therefrom upon said sidewall.

13. The apparatus of claim 1 in which said collector is formed of a rigid polymeric material, said collection cavity, said top wall portion, said lip and said urine collection well being integrally formed together.

14. A method for collecting urine from a human body comprising the steps of:

providing a rigid polymeric collector having a lip configured to surmount the urethra of said body and engage skin adjacent thereto in urine collecting relationship, said collector having a collection cavity with a top wall portion incorporating a vacuum control orifice having an air entry opening, said collector collection cavity having a lower disposed urine collection well generally oppositely disposed from said top wall portion and extending below said lip in fluid flow communication with said collection cavity;

providing a urine collection tank having an internally disposed, normally upstanding sidewall, a urine input port, a vacuum port and a removable upwardly disposed cap;

providing a urine collection conduit having a collection opening within said well and having a urine expulsion end extending through said tank input port, and having at least a transparent region for observing urine flow;

providing a vacuum assembly including a vacuum conduit having an air intake opening extending through said collection tank input port and actuable between on and off conditions to respectively form a vacuum condition and remove said vacuum condition within said collection tank;

actuating said vacuum assembly from said off to said on condition;

positioning said collector lip in an orientation surmounting the urethra of said body wherein said collection cavity top wall portion is generally upwardly disposed and said urine collection well is generally downwardly disposed;

admitting atmospheric air into said collection cavity at the region of said collection cavity top wall portion in an amount effective to effect removal of urine from said urine collection well and to effect a drying of skin located within said lip;

detecting the termination of urination by observing a cessation of urine flow at said urine collection conduit; and actuating said vacuum assembly from said on to said off condition at the termination of urination.

15. The method of claim 14 including the step of collecting urine within said urine collection tank by directing urine from said urine collection conduit expulsion end along and in adjacency with said collection tank internally disposed, normally upstanding sidewall to effect collection of urine while avoiding foam formation within said tank.

16. The method of claim 14 in which said step of actuating said vacuum assembly from said on to said off condition is delayed following said detection of termination of urination for an interval effective to dry skin of said body having had contact with urine.

17. Apparatus for collecting urine from a body, comprising:

a collector having a lip configured to surmount the urethra and engage skin adjacent thereto in urine collecting relationship, a collection cavity extending outwardly from said lip having a normally upwardly disposed top wall portion and including an orifice at said top wall portion having an air entry opening selected to facilitate the passage of atmospheric air in contacting adjacency with the skin adjacent said urethra and having a normally downwardly disposed urine receiving well disposed oppositely from said top wall:

a urine collection tank having an internally disposed normally upstanding side wall, a urine input port, a vacuum port and a removable upwardly disposed cover;

a urine collection conduit having a collection opening positioned at said well for collecting urine from said collector urine receiving well in a substantially liquid state and having a urine expulsion end extending through said urine input port; and a vacuum assembly including a vacuum conduit having an air intake opening extending through said collection tank vacuum port spaced from said urine collection conduit urine expulsion end.

18. The apparatus of claim 17 in which said air entry opening has a first dimensional extent selected to facilitate the positioning of said lip in contacting adjacency with the skin adjacent said urethra which is effective to derive a vacuum within said collection cavity of about 5 kilopascals.

19. The apparatus of claim 17 in which said urine collection conduit is formed of a flexible polymeric material having a transparency effective to permit visual monitoring of the passage of urine therethrough to determine the termination of urine flow.

20. The apparatus of claim 17 in which said urine collection conduit extends within said urine collection tank to an extent wherein said urine expulsion end is below said vacuum assembly air intake opening and at a location in adjacency with said internal sidewall effective to avoid foam formation within said tank.

* * * * *